US012806149B2

(12) United States Patent
Bhavanasi et al.

(10) Patent No.: US 12,806,149 B2
(45) Date of Patent: Nov. 24, 2026

(54) PHARMACEUTICAL COMPOSITIONS COMPRISING ACALABRUTINIB

(71) Applicant: NATCO PHARMA LIMITED, Hyderabad (IN)

(72) Inventors: Krishna Murthy Bhavanasi, Hyderabad (IN); Satyanarayana Vattikuti, Hyderabad (IN); Naveen Krishna Yalamanchalli, Hyderabad (IN); Pavan Bhat, Hyderabad (IN); Venkaiah Chowdary Nannapaneni, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 328 days.

(21) Appl. No.: 18/261,213

(22) PCT Filed: Jan. 10, 2022

(86) PCT No.: PCT/IN2022/050020
§ 371 (c)(1),
(2) Date: Jul. 12, 2023

(87) PCT Pub. No.: WO2022/153330
PCT Pub. Date: Jul. 21, 2022

(65) Prior Publication Data

US 2024/0315978 A1 Sep. 26, 2024

(30) Foreign Application Priority Data

Jan. 13, 2021 (IN) ............................ 202141001568

(51) Int. Cl.
*A61K 9/48* (2006.01)
*A61K 31/4985* (2006.01)

(52) U.S. Cl.
CPC ............ *A61K 9/4858* (2013.01); *A61K 9/485* (2013.01); *A61K 9/4866* (2013.01); *A61K 31/4985* (2013.01)

(58) Field of Classification Search
CPC ............ H04W 74/0833; H04W 72/02; H04W 72/0446; H04W 74/0866
See application file for complete search history.

(56) References Cited

U.S. PATENT DOCUMENTS

| | | | |
|---|---|---|---|
| 9,758,524 | B2 | 9/2017 | Barf et al. |
| 9,796,721 | B2 | 10/2017 | Blatter et al. |
| 10,167,291 | B2 | 1/2019 | Blatter et al. |
| 10,239,883 | B2 | 3/2019 | Barf et al. |
| 10,272,083 | B2 | 4/2019 | Hamdy et al. |
| 2019/0031436 | A1 | 1/2019 | Aggarwala et al. |

FOREIGN PATENT DOCUMENTS

| | | |
|---|---|---|
| WO | 2019041026 A1 | 3/2019 |

OTHER PUBLICATIONS https://www.oed.com/dictionary/metastable_adj?tab=meaning_and_use#37069800 retrieved on Dec. 8, 2025.*
Greco, K.; Bogner, R. Solution-mediated phase transformation: Significant during dissolution and implications for bioavailability. Journal of Pharmaceutical Sciences, vol. 101, No. 9, 2996-3018. (Year: 2012).*

* cited by examiner

*Primary Examiner* — Jessica Worsham
(74) *Attorney, Agent, or Firm* — Dickinson Wright PLLC

(57) ABSTRACT

The present invention relates to pharmaceutical compositions comprising a Bruton tyrosine kinase (BTK) inhibitor. More particularly, the present invention relates to a composition comprising Acalabrutinib or a pharmaceutically acceptable salt thereof and one or more pharmaceutically acceptable excipients and process for preparing such compositions.

3 Claims, No Drawings

PHARMACEUTICAL COMPOSITIONS COMPRISING ACALABRUTINIB

FIELD OF THE INVENTION

The present invention relates to pharmaceutical compositions comprising a Bruton tyrosine kinase (BTK) inhibitor. More particularly, the present invention relates to a composition comprising Acalabrutinib or a pharmaceutically acceptable salt thereof and one or more pharmaceutically acceptable excipients and process for preparing such compositions.

BACKGROUND OF THE INVENTION

Acalabrutinib is an inhibitor of Bruton's tyrosine kinase (BTK). The chemical name for Acalabrutinib is 4-{8-amino-3-[(2S)-1-(but-2-ynoyl) pyrrolidin-2-yl]imidazo[1,5-a]pyrazin-1-yl)}-N-(pyridine-2-yl)benzamide.

Acalabrutinib is approved in the form of capsules and marketed by AstraZeneca under the brand name CALQUENCE®. The Capsules are approved in the strength of 100 mg.

Acalabrutinib is indicated for the treatment of Mantle Cell Lymphoma, Chronic Lymphocytic Leukemia and Small Lymphocytic Lymphoma.

Acalabrutinib is a small-molecule inhibitor of BTK. Acalabrutinib and its active metabolite, ACP-5862, form a covalent bond with a cysteine residue in the BTK active site, leading to inhibition of BTK enzymatic activity.

CALQUENCE® (Acalabrutinib) capsules for oral administration contains 100 mg acalabrutinib and the following inactive ingredients: silicified microcrystalline cellulose, partially pregelatinized starch, magnesium stearate, and sodium starch glycolate. The capsule shell contains gelatin, titanium dioxide, yellow iron oxide, FD&C Blue 2 and is imprinted with edible black ink.

U.S. Pat. No. 9,758,524 discloses a method of treating Mantle Cell Lymphoma (MCL) in a human subject, the method comprising administering Acalabrutinib to the human subject.

U.S. Pat. Nos. 9,796,721 and 10,167,291 discloses a crystalline form I of Acalabrutinib and compositions comprising crystallline form I of Acalabrutinib.

U.S. Pat. No. 10,239,883 discloses a method of treating method of treating chronic lymphocytic leukemia by administering Acalabrutinib.

U.S. Pat. No. 10,272,083 discloses a method of treating chronic lymphocytic leukemia (CLL) or small lymphocytic leukemia (SLL) and mantle cell lymphoma (MCL) by orally administering Acalabrutinib at a dose of 100 mg twice daily.

US 2019/0314369 discloses a method of treating Waldenstrom's macroglobulinemia by administering Acalabrutinib.

The above prior art references disclose different crystalline forms of Acalabrutinib and compositions comprising crystalline Form I of Acalabrutinib. Still, there exists a need to develop an alternative stable dosage form comprising Acalabrutinib. The inventors of the present invention have surprisingly found that a capsule composition comprising crystalline Form III of Acalabrutinib showed comparable dissolution properties, content uniformity, stability and equivalent bioavailability w.r.t commercialized Acalabrutinib capsule dosage form. Further, crystalline Form III of Acalabrutinib does not show any change in polymorphic form even after accelerated stability studies.

Objective of the Invention

The main objective of the present invention relates to a pharmaceutical composition comprising Acalabrutinib or a pharmaceutically acceptable salt thereof.

The present invention also relates to a capsule composition comprising Acalabrutinib and one or more pharmaceutically acceptable excipients.

The present invention also relates to a process for the preparation of capsule composition comprising Acalabrutinib and one or more pharmaceutically acceptable excipients having comparable dissolution properties, content uniformity, stability and equivalent bioavailability w.r.t commercialized Acalabrutinib capsule dosage form.

SUMMARY OF THE INVENTION

Accordingly, the present invention provides a pharmaceutical composition comprising crystalline Form III of Acalabrutinib or a pharmaceutically acceptable salt thereof and one or more pharmaceutically acceptable excipients.

The present invention also relates to a capsule composition comprising crystalline Form III of Acalabrutinib or a pharmaceutically acceptable salt thereof and one or more pharmaceutically acceptable excipients.

DETAILED DESCRIPTION OF THE INVENTION

The present invention relates to a pharmaceutical composition comprising Acalabrutinib or a pharmaceutically acceptable salt thereof and one or more pharmaceutically acceptable excipients.

The present invention further relates to a capsule composition comprising Acalabrutinib or a pharmaceutically acceptable salt thereof and one or more pharmaceutically acceptable excipients.

The present invention also relates to a pharmaceutical composition comprising crystalline Form III of Acalabrutinib or a pharmaceutically acceptable salt thereof and one or more pharmaceutically acceptable excipients.

The present invention also relates to a capsule composition comprising crystalline Form III of Acalabrutinib or a pharmaceutically acceptable salt thereof and one or more pharmaceutically acceptable excipients.

The present invention also relates to a process for preparing a capsule composition comprising crystalline Form III of Acalabrutinib or a pharmaceutically acceptable salt thereof and one or more pharmaceutically acceptable excipients.

The present invention also relates to a stable pharmaceutical composition comprising crystalline Form III of Acalabrutinib or a pharmaceutically acceptable salt thereof and one or more pharmaceutically acceptable excipients.

The present invention also relates to a stable capsule composition comprising crystalline Form III of Acalabrutinib or a pharmaceutically acceptable salt thereof and one or more pharmaceutically acceptable excipients.

In an embodiment, "Acalabrutinib" according to the present invention includes but not limited to Acalabrutinib free base and its pharmaceutically acceptable salts, ethers, esters, prodrugs, polymorphs and derivatives thereof.

In another embodiment, "Acalabrutinib" according to the present invention is in the form of free base.

In another embodiment of the present invention, Acalabrutinib may be present in crystalline form or amorphous form.

In another embodiment of the present invention, Acalabrutinib may be present in crystalline form, preferably in crystalline Form III of Acalabrutinib.

As used herein, the term "% w/w" refers to the weight of the component based on the total weight of a composition comprising the component.

In another embodiment of the present invention, the composition comprises Acalabrutinib in an amount of 20-80% w/w, preferably 30-60% w/w and most preferably 30-50% w/w of the composition.

"Pharmaceutically acceptable excipient/s" are the components added to pharmaceutical formulation to facilitate manufacture, enhance stability, control release, enhance product characteristics, enhance bioavailability, enhance patient acceptability, etc.

In another embodiment, the composition according to the present invention further comprises one or more pharmaceutically acceptable excipients which include but not limited to fillers/diluents, disintegrants, binders, surfactants, polymers, glidants and lubricants. These excipients may be present intragranularly or extragranularly.

Fillers/diluents according to the present invention include but not limited to microcrystalline cellulose, silicified microcrystalline cellulose, lactose monohydrate, lactose anhydrous, fructose, maltose, trehalose, dextrose, polydextrose, dextrates, dextrins, isomalt, mannitol, maltitol, xylitol, maltodextrin, lactitol, sorbitol, erythritol, inulin, starch, pregelatinized starch, sucrose, calcium carbonate, dibasic calcium phosphate, tribasic calcium phosphate, calcium sulfate, magnesium carbonate, magnesium oxide, sodium bicarbonate, sodium carbonate, sodium chloride, cellulose acetate, ethyl cellulose, cellulose powdered, kaolin and the like or combinations thereof. The fillers/diluents can be used in the range of about 0-90% w/w of the composition.

Disintegrants according to the present invention include but not limited to starches or modified starches such as pregelatinized starch, croscarmellose sodium, carmellose sodium, carmellose calcium, povidone (polyvinyl pyrrolidone), copovidone, crospovidone (Crosslinked polyvinyl pyrrolidone), sodium starch glycolate, low substituted hydroxypropyl cellulose, hydroxypropyl cellulose, alginic acid, and the like or combinations thereof. The disintegrant can be used in the range of about 0-25% w/w of the composition.

Binders according to the present invention include but not limited to hydroxypropyl methylcellulose (Hypromellose), hydroxypropyl cellulose, gelatin, ethyl cellulose, polyvinyl alcohol, pregelatinized starch, carboxymethyl cellulose, sodium alginate, polyvinyl pyrrolidones (povidone), copovidone, microcrystalline cellulose, gelatin, polymethacrylates, polyethylene glycols (PEG), Poly(vinyl caprolactam-co-vinyl acetate-ethylene glycol) graft polymer (SOLUPLUS®), poloxamers, polyethylene oxide, acrylate based copolymers and the like or combinations thereof. The binder can be used in the range of about 0-15% w/w of the composition.

Surfactants according to the present invention may be selected from anionic, cationic or non-ionic surface-active agents or surfactants. Suitable anionic surfactants include but not limited to carboxylate, sulfonate, and sulfate ions such as sodium lauryl sulfate (SLS), sodium laurate, dialkyl sodium sulfosuccinates particularly bis-(2-ethylhexyl) sodium sulfosuccinate, sodium stearate, potassium stearate, sodium oleate and the like. Suitable cationic surfactants include but not limited to those containing long chain cations, such as benzalkonium chloride, bis-2-hydroxyethyl oleyl amine or the like. Suitable non-ionic surfactants include but not limited to polyoxyethylene sorbitan fatty acid esters (polysorbates), fatty alcohols such as lauryl, cetyl and stearyl alcohols; glyceryl esters such as the naturally occurring mono-, di-, and tri-glycerides; fatty acid esters of fatty alcohols; polyglycolized glycerides such as gelucire; polyoxyethylene-polyoxypropylene block co-polymer such as Poloxamer and other alcohols such as propylene glycol, polyethylene glycol. The surfactant can be used in the range of about 0-20% w/w of the composition.

Polymers according to the present invention include but not limited to hydroxypropyl cellulose, hydroxypropylmethyl cellulose, methyl cellulose, propylene glycol alginate ester, sodium caseinate, a carboxyvinyl polymer, powdered agar, guar gum, copolyvidone, hydroxyethylmethyl cellulose, or polyvinyl alcohol, the gastric-soluble polymer is amino alkylmethacrylate copolymer E, or polyvinylacetal diethylaminoacetate, and the enteric-soluble polymer is methacrylic acid copolymer LD, purified shellac, carboxymethylethyl cellulose, cellulose acetate phthalate, hydroxypropylmethyl cellulose acetate succinate, methacrylic acid copolymer S, casein, zein and mixtures thereof. The polymer can be used in the range of about 0-60% w/w of the composition.

Glidants according to the present invention include but not limited to silica, colloidal silicon dioxide, talc and magnesium silicate and mixtures thereof. The glidants can be used in the range of 0-10% w/w of the composition.

Lubricants according to the present invention include but not limited to stearic acid, magnesium stearate, calcium stearate, sodium stearyl fumarate, talc, zinc stearate, glyceryl mono fatty acid, glyceryl monostearate, glyceryl dibehenate, glyceryl palmito stearic ester, hydrogenated castor oil and mixtures thereof. The Lubricants and/or glidants can be used in the range of 0-10% w/w of the composition.

In another embodiment, the present invention relates to a process for the preparation of pharmaceutical composition, comprising the steps of:

(i) blending Acalabrutinib or a pharmaceutically acceptable salt thereof with one or more pharmaceutically acceptable excipients,
(ii) formulating the blend of step (i) into suitable dosage form.

In another embodiment, the present invention relates to a process for the preparation of pharmaceutical composition, comprising the steps of:

(i) blending Acalabrutinib or a pharmaceutically acceptable salt thereof with one or more pharmaceutically acceptable excipients,
(ii) optionally, lubricating the blended material of step (i) with a lubricant, and
(iii) preparing the lubricated material of step (ii) into a suitable dosage form.

In another embodiment, the present invention relates to a process for the preparation of pharmaceutical composition, comprising the steps of:

(i) blending Acalabrutinib or a pharmaceutically acceptable salt thereof with one or more pharmaceutically acceptable excipients,
(ii) optionally, lubricating the blended material of step (i) with a lubricant, and
(iii) filling the lubricated material of step (ii) into capsules.

In another embodiment, the present invention relates to a process for the preparation of pharmaceutical composition, comprising the steps of:

(i) blending Acalabrutinib or a pharmaceutically acceptable salt thereof with one or more pharmaceutically acceptable excipients, (ii) granulating the blend of step (i),
(iii) blending the granules of step (ii) with one or more pharmaceutically acceptable excipients, and
(iii) filling the blend of step (i) into capsules.

In another embodiment, the present invention relates to a process for the preparation of pharmaceutical composition, comprising the steps of:
(i) blending crystalline Form III of Acalabrutinib or a pharmaceutically acceptable salt thereof with one or more pharmaceutically acceptable excipients,
(ii) formulating the blend of step (i) into suitable dosage form.

In another embodiment, the present invention relates to a process for the preparation of pharmaceutical composition, comprising the steps of:
(i) blending crystalline Form III of Acalabrutinib or a pharmaceutically acceptable salt thereof with one or more pharmaceutically acceptable excipients,
(ii) optionally, lubricating the blended material of step (i) with a lubricant, and
(iii) preparing the lubricated material of step (ii) into a suitable dosage form.

In another embodiment, the present invention relates to a process for the preparation of pharmaceutical composition, comprising the steps of:
(i) blending crystalline Form III of Acalabrutinib or a pharmaceutically acceptable salt thereof with one or more pharmaceutically acceptable excipients,
(ii) optionally, lubricating the blended material of step (i) with a lubricant, and
(iii) filling the lubricated material of step (ii) into capsules.

In another embodiment, the present invention relates to a process for the preparation of pharmaceutical composition, comprising the steps of:
(i) blending crystalline Form III of Acalabrutinib or a pharmaceutically acceptable salt thereof with one or more pharmaceutically acceptable excipients,
(ii) granulating the blend of step (i),
(iii) blending the granules of step (ii) with one or more pharmaceutically acceptable excipients, and
(iii) filling the blend of step (i) into capsules.

In another embodiment, the present invention relates to a process for the preparation of stable capsule composition, comprising the steps of:
(i) blending crystalline Form III of Acalabrutinib with a diluent, disintegrant and a glidant,
(ii) lubricating the blend of step (i) with a lubricant,
(iii) granulating the lubricated blend of step (ii) by roller compaction,
(iv) lubricating the blend of step (iii) with extragranular lubricant,
(vi) filling the lubricated blend of step (iv) into capsules.

In another embodiment, the present invention relates to a process for the preparation of stable capsule composition, comprising the steps of:
(i) blending crystalline Form III of Acalabrutinib with mannitol, croscarmellose sodium and colloidal silicon dioxide,
(ii) lubricating the blend of step (i) with sodium stearyl fumarate,
(iii) granulating the lubricated blend of step (ii) by roller compaction,
(iv) lubricating the blend of step (iii) with extragranular sodium stearyl fumarate,
(vi) filling the lubricated blend of step (iv) into capsules.

In another embodiment, the present invention relates to a capsule composition comprising:
(i) Acalabrutinib or a pharmaceutically acceptable salt thereof,
(ii) at least one diluent,
(iii) at least one disintegrant,
(iv) at least one glidant and
(v) at least one lubricant.

In another embodiment, the present invention relates to a capsule composition comprising:
(i) Acalabrutinib or a pharmaceutically acceptable salt thereof,
(ii) at least one diluent selected from mannitol, microcrystalline cellulose and lactose,
(iii) at least one disintegrant selected from sodium starch glycolate, crospovidone and croscarmellose sodium,
(iv) at least one glidant selected from colloidal silicon dioxide and talc and
(v) at least one lubricant selected from magnesium stearate and sodium stearyl fumarate.

In another embodiment, the present invention relates to a capsule composition comprising:
(i) 30-50% w/w of Acalabrutinib or a pharmaceutically acceptable salt thereof,
(ii) 20-80% w/w of at least one diluent,
(iii) 5-20% w/w of at least one disintegrant,
(iv) 0.5-5% w/w of at least one glidant and
(v) 0.5-5% w/w of at least one lubricant.

In another embodiment, the present invention relates to a capsule composition comprising:
(i) 30-50% w/w of crystalline Form III of Acalabrutinib or a pharmaceutically acceptable salt thereof,
(ii) 20-80% w/w of at least one diluent selected from mannitol, microcrystalline cellulose and lactose,
(iii) 5-20% w/w of at least one disintegrant selected from sodium starch glycolate, crospovidone and croscarmellose sodium,
(iv) 0.5-5% w/w of at least one glidant selected from colloidal silicon dioxide and talc and
(v) 0.5-5% w/w of at least one lubricant selected from magnesium stearate and sodium stearyl fumarate.

In another embodiment, the present invention relates to a capsule composition comprising:
(i) 30-50% w/w of crystalline Form III of Acalabrutinib or a pharmaceutically acceptable salt thereof,
(ii) 20-80% w/w of mannitol,
(iii) 5-20% w/w of croscarmellose sodium,
(iv) 0.5-5% w/w of colloidal silicon dioxide and
(v) 0.5-5% w/w of sodium stearyl fumarate.

In another embodiment, the present invention relates to a capsule composition comprising:
(i) 30-50% w/w of crystalline Form III of Acalabrutinib or a pharmaceutically acceptable salt thereof,
(ii) 20-80% w/w of lactose,
(iii) 5-20% w/w of croscarmellose sodium,
(iv) 0.5-5% w/w of colloidal silicon dioxide and
(v) 0.5-5% w/w of sodium stearyl fumarate.

In another embodiment, the present invention relates to a capsule composition of Acalabrutinib prepared by a process comprising the steps of:
(i) blending crystalline Form III of Acalabrutinib with a diluent, disintegrant and a glidant,
(ii) lubricating the blend of step (i) with a lubricant,
(iii) granulating the lubricated blend of step (ii) by roller compaction,
(iv) lubricating the blend of step (iii) with extragranular lubricant,
(v) filling the lubricated blend of step (iv) into capsules.

In another embodiment, the present invention relates to a capsule composition of Acalabrutinib prepared by a process comprising the steps of:

(i) blending crystalline Form III of Acalabrutinib with mannitol, croscarmellose sodium and colloidal silicon dioxide,
(ii) lubricating the blend of step (i) with sodium stearyl fumarate,
(iii) granulating the lubricated blend of step (ii) by roller compaction,
(iv) lubricating the blend of step (iii) with extragranular sodium stearyl fumarate,
(v) filling the lubricated blend of step (iv) into capsules.

In another embodiment, the pharmaceutical composition according to the present invention is in the form of tablets, capsules, granules, powder, pellets and sachets.

In one preferred embodiment, the pharmaceutical composition according to the present invention is in the form of capsules including but not limited to soft gelatin, hard gelatin, HPMC, polysaccharide or starch capsules as plugged, welded or glued capsules, of different size, colour, and water content.

In another preferred embodiment, the pharmaceutical composition according to the present invention is in the form of hard gelatin capsules.

In another preferred embodiment, the capsules are selected from hard gelatin capsules of Size 1.

In another preferred embodiment, the present invention relates to a capsule composition comprising crystalline Form III of Acalabrutinib, wherein the total fill weight of the capsule is less than 500 mg, preferable less than 400 mg and more preferably less than 300 mg.

In another embodiment, the blend is formulated into a suitable dosage form like tablets or capsules using different techniques which are well known in the prior art.

In another embodiment, the compositions of the present invention may be prepared using any method known in the art, but are not limited to wet granulation, melt granulation, dry granulation, roller compaction, solid dispersion, encapsulation and direct compression.

In another embodiment, the granulation can be done using one pharmaceutically acceptable excipient, a binder, which can be added to the drug substance in a dissolved state (e.g. in an aqueous/non-aqueous solution) or in a powder form and then granulated by adding a granulation liquid. A combination of more than one binder can be used.

In another embodiment, the solvents used for granulation process may be selected from water, isopropyl alcohol, methanol, ethanol, methylene chloride or combination thereof.

In another embodiment, the granulation can be done using any method known in the art, but are not limited to fluidized bed granulation, high-shear granulation, low shear granulation, spray granulation, melt granulation and hot melt extrusion.

The pharmaceutical composition may be further film coated with functional or non functional layer. The coating may be selected from amongst one or more of those suitable coating materials known in the art. For example, the coating material can be Opadry or Opadry AMB. Coating may be performed by applying one or more film forming polymers, with or without other pharmaceutically inert excipients, as a solution/suspension using any conventional coating technique known in the art, such as spray coating in a conventional coating pan or fluidized bed processor; or dip coating.

Coloring agent may be selected from FDA approved colorants such as Iron Oxide, Lake of Tartrazine, Allura Red, Lake of Quinoline Yellow, Lake of Erythrosine, Titanium Dioxide and the like.

In another embodiment, the present invention provides a capsule composition comprising crystalline Form III of Acalabrutinib or a pharmaceutically acceptable salt thereof in the range of about 1 mg to about 500 mg, preferably 50 mg to 200 mg and more preferably 100 mg.

In another embodiment, the present invention provides a capsule composition comprising crystalline Form III of Acalabrutinib or a pharmaceutically acceptable salt thereof for the treatment of patients with Mantle Cell Lymphoma, Chronic Lymphocytic Leukemia and Small Lymphocytic Lymphoma.

As used herein, the term "stable" means less than 1% of known and/or unknown impurities and less than 5% of total impurities.

In another embodiment, the present invention provides a stable capsule composition comprising crystalline Form III of Acalabrutinib, and the capsule composition is chemically stable when stored at 40±2° C./75±5% RH for 6 months.

In another embodiment, the present invention provides a stable capsule composition comprising crystalline Form III of Acalabrutinib, wherein there is no change in polymorphic form when stored at 40±2° C./75±5% RH for 6 months.

In another embodiment, the present invention provides a stable capsule composition comprising crystalline Form III of Acalabrutinib, said capsule comprising not more than about 1% of known impurities, not more than about 0.5% of any individual unknown impurity and not more than about 4% of total impurities when stored at 40±2° C./75±5% RH for 6 months.

In another preferred embodiment, the present invention provides a stable capsule composition comprising crystalline Form III of Acalabrutinib, said capsule comprising not more than about 0.5% of known impurities, not more than about 0.3% of any individual unknown impurity and not more than about 1% of total impurities when stored at 40±2° C./75±5% RH for 6 months.

In another embodiment, the present invention provides a stable capsule composition comprising crystalline Form III of Acalabrutinib, having a moisture content/water content in the range of 0-8% w/w, preferably in the range of 0-5% w/w and more preferably in the range of 0-3% w/w.

In another embodiment, the present invention provides a stable capsule composition comprising crystalline Form III of Acalabrutinib, having assay in the range of 95.0% to 105.0%.

In another embodiment, the present invention provides a stable capsule composition comprising crystalline Form III of Acalabrutinib, having a dissolution not less than 75% of the labeled amount of Acalabrutinib in 30 minutes.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1: Capsule Composition Comprising Acalabrutinib

| S. No | Ingredients | Quantity (mg/cap) |
|---|---|---|
| | Intra-granular | |
| 1 | Acalabrutinib | 100.00 |
| 2 | Lactose | 142.80 |
| 3 | Croscarmellose sodium | 29.40 |
| 4 | Colloidal silicon dioxide | 1.40 |
| | Extra-granular | |
| 5 | Colloidal silicon dioxide | 1.40 |
| 6 | Sodium stearyl fumarate | 5.00 |
| | Total Capsule fill weight | 280.00 |

The processing steps involved in manufacturing the capsules were given below:

(i) Acalabrutinib, Lactose, Croscarmellose sodium and Colloidal silicon dioxide were sifted separately and blended, (ii) the blend of step (i) was compacted using a roller compacted and milled, (iii) the granules obtained in step (ii) were blended with extra-granular Colloidal silicon dioxide, (iv) the blend of step (iii) was lubricated with Sodium stearyl fumarate, (v) the lubricated granules of step (iv) were filled into capsules.

Example 2: Capsule Composition Comprising Acalabrutinib

| S. No | Ingredients | Quantity (mg/cap) |
|---|---|---|
| | Intra-granular | |
| 1 | Acalabrutinib | 100.00 |
| 2 | Mannitol | 142.80 |
| 3 | Croscarmellose sodium | 29.40 |
| 4 | Colloidal silicon dioxide | 1.40 |
| | Extra-granular | |
| 5 | Colloidal silicon dioxide | 1.40 |
| 6 | Sodium stearyl fumarate | 5.00 |
| | Total Capsule fill weight | 280.00 |

Example 3: Capsule Composition Comprising Acalabrutinib

| S. No | Ingredients | Quantity (mg/cap) |
|---|---|---|
| | Intra-granular | |
| 1 | Acalabrutinib | 100.00 |
| 2 | Mannitol | 71.00 |
| 3 | Croscarmellose sodium | 21.20 |
| 4 | Colloidal silicon dioxide | 1.40 |
| | Extra-granular | |
| 5 | Colloidal silicon dioxide | 1.40 |
| 6 | Sodium stearyl fumarate | 5.00 |
| | Total Capsule fill weight | 200.00 |

Example 4: Capsule Composition Comprising Acalabrutinib

| S. No | Ingredients | Quantity (mg/cap) |
|---|---|---|
| | Intra-granular | |
| 1 | Acalabrutinib | 100.00 |
| 2 | Mannitol | 146.40 |
| 3 | Croscarmellose sodium | 28.00 |
| 4 | Colloidal silicon dioxide | 2.80 |
| 5 | Sodium stearyl fumarate | 1.40 |
| | Extra-granular | |
| 6 | Sodium stearyl fumarate | 1.40 |
| | Total Capsule fill weight | 280.00 |

Example 5: Capsule Composition Comprising Acalabrutinib

| S. No | Ingredients | Quantity (mg/cap) |
|---|---|---|
| | Intra-granular | |
| 1 | Acalabrutinib | 100.00 |
| 2 | Lactose | 146.40 |
| 3 | Croscarmellose sodium | 28.00 |
| 4 | Colloidal silicon dioxide | 2.80 |
| 5 | Sodium stearyl fumarate | 1.40 |
| | Extra-granular | |
| 6 | Sodium stearyl fumarate | 1.40 |
| | Total Capsule fill weight | 280.00 |

The process involved in manufacturing the capsules of Examples 2-5 is similar to the process provided in Example 1.

Example 6: Capsule Composition Comprising Acalabrutinib Dihydrate (Crystalline Form III)

| S. No | Ingredients | Quantity (mg/cap) |
|---|---|---|
| | Intra-granular | |
| 1 | Acalabrutinib dihydrate* | 107.74 |
| 2 | Mannitol | 136.46 |
| 3 | Croscarmellose sodium | 28.00 |
| 4 | Colloidal silicon dioxide | 2.80 |
| 5 | Sodium stearyl fumarate | 2.50 |

-continued

| S. No | Ingredients | Quantity (mg/cap) |
|---|---|---|
| | Extra-granular | |
| 6 | Sodium stearyl fumarate | 2.50 |
| | Total Capsule fill weight | 280.00 |
| 7 | Capsules | Size 1 |

*Note:

107.74 mg of Acalabrutinib dihydrate is equivalent to 100 mg of Acalabrutinib.

The processing steps involved in manufacturing the capsules were given below:

(i) Acalabrutinib dihydrate, Mannitol, Croscarmellose sodium, Colloidal silicon dioxide and Sodium stearyl fumarate were sifted separately and blended, (ii) the blend of step (i) was compacted using a roller compacted and milled, (iii) the granules obtained in step (ii) were lubricated with Sodium stearyl fumarate, (iv) the lubricated granules of step (iii) were filled into capsules.

Dissolution Data: Table 1 given 5 below provides the comparative dissolution profile of Acalabrutinib capsules 100 mg prepared according to Example 6 with CALQUENCE® (Acalabrutinib) capsules in 900 ml of 0.1N HCl as dissolution medium in USP II apparatus (paddle) with sinker at 50 rpm.

TABLE 1

Comparative dissolution profile of Acalabrutinib capsules 100 mg prepared according to Example 6 with CALQUENCE (Acalabrutinib) capsules

| | Cumulative % drug released | |
|---|---|---|
| Time (in min) | CALQUENCE (Acalabrutinib) capsules | Acalabrutinib capsules 100 mg prepared according to Example 6 |
| 5 | 66 | 88 |
| 10 | 100 | 100 |
| 15 | 102 | 101 |
| 20 | 101 | 101 |
| 30 | 101 | 101 |
| 45 | 101 | 101 |

Based on the above data more than 85% release was observed within 15 minutes in both Acalabrutinib capsules 100 mg prepared according to Example 6 and CALQUENCE (Acalabrutinib) capsules 100 mg. Hence, it was concluded that the dissolution profile of Acalabrutinib capsules 100 mg prepared according to Example 6 was comparable with CALQUENCE® (Acalabrutinib) capsules 100 mg.

Stability Data:

Table 2 given below shows the impurity profile of Acalabrutinib capsules 100 mg prepared according to Example 6 of the present invention after storing at 40±2° C./75±5% RH for 6 months.

TABLE 2

Stability data of Acalabrutinib capsules 100 mg prepared according to Example 6 after storing in HDPE bottles at 40 ± 2° C./75 ± 5% RH for 6 months

| Characteristics | Initial | 1st month | 3rd month | 6th month |
|---|---|---|---|---|
| Assay | 102.6% | 102.6% | 103.8% | 102.7% |
| Moisture content | 2.8% | 3.3% | 3.4% | 3.6% |
| Total Impurities | 0.14% | 0.34% | 0.55% | 0.90% |

The above stability study results of the Acalabrutinib capsules 100 mg prepared according to Example 6 indicates that, the capsules remain stable for a period of 6 months even after storing at 40±2° C./75±5% RH for 6 months. Further, total impurities were within the specified limits.

Table 3 given below shows the impurity profile of Acalabrutinib capsules 100 mg prepared according to Example 6 of the present invention after storing at 30±2° C./75±5% RH for 6 months.

TABLE 2

Stability data of Acalabrutinib capsules 100 mg prepared according to Example 6 after storing in HDPE bottles at 30 ± 2° C./75 ± 5% RH for 6 months

| Characteristics | Initial | 3rd month | 6th month |
|---|---|---|---|
| Assay | 101.8% | 101.1% | 101.7% |
| Moisture content | 3.0% | 3.4% | 3.3% |
| Total Impurities | 0.14% | 0.21% | 0.36% |

The above stability study results of the Acalabrutinib capsules 100 mg prepared according to Example 6 indicates that the capsules remain stable for a period of 6 months even after storing at 30±2° C./75±5% RH for 6 months. Further, total impurities were within the specified limits.

We claim:

1. A stable capsule composition comprising crystalline Form III of Acalabrutinib or a pharmaceutically acceptable salt thereof and one or more pharmaceutically acceptable excipients, wherein the composition comprises:

(i) 30-50% w/w of crystalline Form III of Acalabrutinib or a pharmaceutically acceptable salt thereof, (ii) 20-80% w/w of a diluent wherein the diluent is mannitol, (iii) 5-20% w/w of a disintegrant wherein the disintegrant is croscarmellose sodium, (iv) 0.5-5% w/w of a glidant wherein the glidant is colloidal silicon dioxide, and (v) 0.5-5% w/w of a lubricant wherein the lubricant is sodium stearyl fumarate.

2. The stable capsule composition as claimed in claim 1, wherein the composition is prepared by wet granulation, melt granulation, dry granulation, roller compaction, solid dispersion and encapsulation.

3. The stable capsule composition as claimed in claim 1, wherein the composition is prepared by a process comprising the steps of:

(i) blending crystalline Form III of Acalabrutinib with mannitol, croscarmellose sodium and colloidal silicon dioxide, (ii) lubricating the blend of step (i) with sodium stearyl fumarate, (iii) granulating the lubricated blend of step (ii) by roller compaction,
(iv) lubricating the blend of step (iii) with extragranular sodium stearyl fumarate,
(v) filling the lubricated blend of step (iv) into capsules.

* * * * *